(12) United States Patent
Smith et al.

(10) Patent No.: US 11,918,826 B2
(45) Date of Patent: Mar. 5, 2024

(54) SYSTEM AND METHOD FOR MODULATING OPTOGENETIC VAGUS NERVE IN A NONINVASIVE, TRANSCUTANEOUS MANNER

(71) Applicant: Arizona Board of Regents on behalf of Arizona State University, Scottsdale, AZ (US)

(72) Inventors: Joseph T. Smith, Tempe, AZ (US); Michael Goryll, Mesa, AZ (US); Dixie Kullman, Casa Grande, AZ (US); Jitendran Muthuswamy, Chandler, AZ (US); Jennifer Blain Christen, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 244 days.

(21) Appl. No.: 17/225,711

(22) Filed: Apr. 8, 2021

(65) Prior Publication Data
US 2021/0220668 A1    Jul. 22, 2021

Related U.S. Application Data

(62) Division of application No. 15/086,800, filed on Mar. 31, 2016, now Pat. No. 10,974,065.
(Continued)

(51) Int. Cl.
*A61N 5/06*    (2006.01)
(52) U.S. Cl.
CPC ......... *A61N 5/0622* (2013.01); *A61N 5/0618* (2013.01); *A61N 2005/0626* (2013.01);
(Continued)

(58) Field of Classification Search
CPC ............... A61N 5/0622; A61N 5/0618; A61N 2005/0626; A61N 2005/0652; A61N 2005/0653; A61N 2005/0663
See application file for complete search history.

(56) References Cited

U.S. PATENT DOCUMENTS

| 2005/0177093 | A1* | 8/2005 | Barry ................. A61N 5/0616 604/20 |
| 2009/0093403 | A1 | 4/2009 | Zhang |

(Continued)

OTHER PUBLICATIONS

Allen, Photoplethysmography and its application in clinical physiological measurement., Physiological Measurement, Mar. 2007, 28(3):R1-R39.
(Continued)

*Primary Examiner* — Brian T Gedeon
*Assistant Examiner* — Joshua Andrew Schum-Houck
(74) *Attorney, Agent, or Firm* — Quarles & Brady, LLP; Yakov Sidorin (57) ABSTRACT

A system and method for modulating optogenetic vagus neurons in a noninvasive and transcutaneous manner is disclosed. The system and method comprises a two-dimensional array of organic light emitting diodes (OLEDs), a voltage-generating unit, a control unit, and a feedback loop. The array is placed on a subject's outer ear. Because the array is flexible, it can be closely placed on the skin of the outer ear. The array can deliver optical therapy and monitor heart rate variability (HRV) of the subject simultaneously, and the pixels of the array can be individually addressed. The voltage-generating unit generates pulsed voltage to the OLEDs. The control unit is connected to the array and controls the array and therapeutic patterns. The feedback loop uses the HRV to identify the therapeutic patterns.

11 Claims, 9 Drawing Sheets

Related U.S. Application Data (60) Provisional application No. 62/141,729, filed on Apr. 1, 2015.

(52) U.S. Cl.
CPC .......... *A61N 2005/0652* (2013.01); *A61N 2005/0653* (2013.01); *A61N 2005/0663* (2013.01)

(56) References Cited

U.S. PATENT DOCUMENTS

| | | | |
|---|---|---|---|
| 2010/0217102 A1* | 8/2010 | LeBoeuf | A61B 5/14532 600/310 |
| 2011/0046432 A1 | 2/2011 | Simon | |
| 2011/0054569 A1 | 3/2011 | Zitnik | |
| 2013/0019325 A1* | 1/2013 | Deisseroth | A61N 5/062 435/325 |
| 2013/0060098 A1 | 3/2013 | Thomsen | |
| 2014/0180039 A1 | 6/2014 | LeBoeuf | |
| 2015/0057512 A1 | 2/2015 | Kapoor | |
| 2015/0073505 A1 | 3/2015 | Errico | |
| 2015/0182129 A1 | 7/2015 | Colley | |
| 2015/0283398 A1 | 10/2015 | Andersen | |
| 2017/0000371 A1 | 1/2017 | Quinlan | |
| 2017/0095670 A1 | 4/2017 | Ghaffari | |
| 2017/0136264 A1 | 5/2017 | Hyde | |
| 2018/0028809 A1 | 2/2018 | Ziv | |
| 2018/0085580 A1 | 3/2018 | Perez | |

OTHER PUBLICATIONS

Darpa, ElectRx Has the Nerve to Envision Revolutionary Therapies for Self-Healing, Darpa.mil, 2014, http://www.darpa.mil/news-events/2014-12-11, retrieved Apr. 4, 2016.

Degenaar et al., Individually addressable optoelectronic arrays for optogenetic neural stimulation., 2010 Biomedical Circuits and Systems Conference (BioCAS), 2010, pp. 170-173.

Deisseroth, Optogenetics, Nature Methods, Jan. 2011, 8(1):26-29.

Eversmann et al., A 128 x 128 CMOS biosensor array for extracellular recording of neural activity., IEEE Journal of Solid-State Circuits, Dec. 2003, 38(12):2306-2317.

Frangos et al., Non-invasive Access to the Vagus Nerve Central Projections via Electrical Stimulation of the External Ear: fMRI Evidence in Humans., Brain stimulation, May 2015, 8(3):624-636.

Gudmundsson, Intracranial Pressure and the Role of the Vagus Nerve: A Hypothesis., World Journal of Neuroscience, 2014, 4:164-169.

Haq et al., Temporary bond-debond process for manufacture of flexible electronics: Impact of adhesive and carrier properties on performance., Journal of Applied Physics, 2010, 108(11):114917(1-7).

Henry, Therapeutic mechanisms of vagus nerve stimulation., Neurology, Sep. 2002, 59(6):S3-S14.

Huston et al., The pulse of inflammation: heart rate variability, the cholinergic anti-inflammatory pathway and implications for therapy., Journal of Internal Medicine, Jan. 2011, 269(1):45-53.

Kim et al., Injectable, cellular-scale optoelectronics with applications for wireless optogenetics., Science, Apr. 2013, 340 (6129):211-216.

Klapoetke et al., Independent optical excitation of distinct neural populations., Nature Methods, Mar. 2014, 11 (3):338-346.

Lochner et al., All-organic optoelectronic sensor for pulse oximetry., Nature Communications, Dec. 2014, 5:5745 (1-7).

Nakanotani et al., Injection and Transport of High Current Density over 1000 A/cm2 in Organic Light Emitting Diodes under Pulse Excitation., Japanese Journal of Applied Physics, Jun. 2005, 44(6A):3659-3662.

O'Brien et al., 14.7? active matrix PHOLED displays on temporary bonded PEN substrates with low temperature IGZO TFTs., Digest of Technical Papers—SID International Symposium, 2013, 44(1):447-450.

Raupp et al., Low-temperature amorphous-silicon backplane technology development for flexible displays in a manufacturing pilot-line environment., Journal of the Society for Information Display, Jul. 2007, 15(7):445-454.

Rong et al., Transcutaneous vagus nerve stimulation for the treatment of depression: A study protocol for a double plinded randomized clinical trial., BMC Complementary and Alternative Medicine, Dec. 2012, 12(1):255(1-6).

Schafer et al., How accurate is pulse rate variability as an estimate of heart rate variability ?: A review on studies comparing photoplethysmographic technology with an electrocardiogram., International Journal of Cardiology, Jun. 2013, 166(1):15-29.

Smith et al., Application of Flexible OLED Display Technology for Electro-Optical Stimulation and/or Silencing of Neural Activity., Journal of Display Technology, 2014, 10(6):514-520.

Smith et al., Flexible ISFET Biosensor Using IGZO Metal Oxide TFTs and an ITO Sensing Layer., IEEE Sensors Journal, 2014, 14(4):937-938.

Smith et al., Optogenetic Neurostimulation of the Auricular Vagus using Flexible OLED Display Technology to Treat Chronic Inflammatory Disease and Mental Health Disorders., Electronic Letters, Mar. 2016, DOI: 10.1049/el.2015.3450.

Suzuki et al., Development of the irregular pulse detection method in daily life using wearable photoplethysmographic sensor., 2009 Annual International Conference of the IEEE Engineering in Medicine and Biology Society, 2009, 6080-6083.

Tracey, Shock Medicine: Stimulation of the nervous system could replace drugs for inflammatory and autoimmune conditions., Scientific American, Mar. 2015, 312(3):28-35.

Tracey, The inflammatory reflex., Nature, Dec. 2002, 420(6917):853-859.

Wagner et al., Materials for stretchable electronics., MRS Bulletin, Mar. 2012, 37(3):207-213.

Wilkinson et al., Enhanced performance of pulse driven small area polyfluorene light emitting diodes., Applied Physics Letters, Jul. 2001, 79(2):171-173.

\* cited by examiner

SYSTEM AND METHOD FOR MODULATING OPTOGENETIC VAGUS NERVE IN A NONINVASIVE, TRANSCUTANEOUS MANNER

CROSS-REFERENCE TO RELATED APPLICATIONS

This application is a divisional of U.S. patent application Ser. No. 15/086,800, filed Mar. 31, 2016, which claims priority to U.S. Provisional Patent Application No. 62/141,729, filed Apr. 1, 2015, each of which is incorporated herein by reference as if set forth in its entirety.

STATEMENT REGARDING FEDERALLY SPONSORED RESEARCH

N/A

BACKGROUND

A surprisingly large number of common chronic inflammatory diseases and mental health disorders—including rheumatoid arthritis, systemic inflammatory response syndrome, inflammatory bowel disease, post-traumatic stress disorder (PTSD), anxiety, depression, and epilepsy—are related to abnormal activity in the peripheral nervous system. As an alternative to conventional treatment using drugs or invasive surgery, targeted regulation of peripheral nerves is promising in helping patients restore and maintain their health. However, existing peripheral neuromodulation devices are typically used as a last resort to medical professionals because those devices are relatively large and often produce undesirable side effects from lack of precision and required invasive surgery.

Therefore, a noninvasive precise neuromodulation device is needed.

SUMMARY

The present disclosure overcomes the aforementioned drawbacks by providing a system and method that modulate the optogenetic auricular vagus nerve in a non-invasive and transcutaneous manner using an array of organic light emitting diodes (OLEDs). The array is flexible and can be placed closely on the skin of a subject's outer ear. The array delivers light to modulate the neurons of the vagus nerve. The pixels of the array are individually addressable to achieve desired specificity. The precision of the modulation is monitored with the heart rate variability (HRV) measured by the same array by using the HRV as feedback in identifying the light patterns delivered by the array.

A system and method for modulating optogenetic vagus neurons in a noninvasive and transcutaneous manner is disclosed. The system and method comprises a two-dimensional array of OLEDs, a voltage-generating unit, a control unit, and a feedback loop. The array is placed on a subject's outer ear. Because the array is flexible, it can be closely placed on the skin of the outer ear. The array can deliver optical therapy and monitor HRV of the subject simultaneously, and the pixels of the array can be individually addressed. The voltage-generating unit generates pulsed voltage to the OLEDs. The control unit is connected to the array and controls the array and therapeutic patterns. The feedback loop uses the HRV to identify the therapeutic patterns.

In one configuration, the array is low-cost and mass-produced so that the system is cheap to consumers and disposable.

In one configuration, the measured HRV is insensitive to motion.

In one configuration, the array is manufactured in a way that the array is flexible with its electronic components intact. In one configuration, polyimide substrate is used in manufacturing the array.

The foregoing and other advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Direct vagus nerve stimulation (VNS) can be used to treat both mental health disorders and inflammatory disease. For noninvasive neuromodulation-based therapies, the outer ear is the only location on the human body where afferent vagus nerves are accessible transcutaneously. Transcutaneous VNS methods using an electrical transducer attached to the outer ear have been attempted to stimulate the auricular vagus nerves electrically. However, those methods and devices lack the specificity required to activate vagus nerves in the outer ear.

The system and method as disclosed herein can optically stimulate the neurons in the auricular vagus nerves with high precision in a noninvasive, transcutaneous manner. It delivers a high precision noninvasive optogenetics-based vagus nerve stimulation (VNS) therapy that is able to optically stimulate or silence auricular vagus nerves in the outer ear using a high resolution two-dimensional (2D) addressable array of organic light emitting diodes (OLEDs) manufactured on a thin and mechanically compliant substrate.

Figure 1:
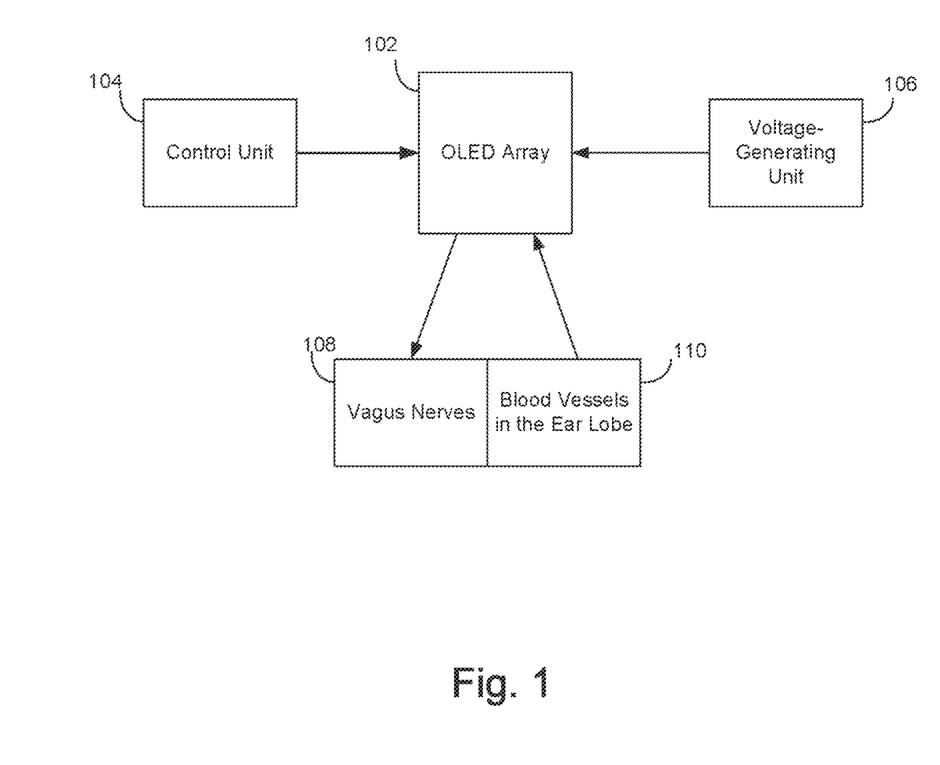
FIG. 1 is a schematic diagram of an example system configured in accordance with the present application.

Referring to FIG. 1, a system implemented according to the present application is provided. An OLED array 102 emits light that stimulates vagus nerves 108. The array 102 is powered by pulsed voltage generated by voltage-generating unit 106. The emitted light is controlled by control unit 104. In some cases, control unit 104 is connected to voltage-generating unit 106 to control delivery of pulsed electrical signals to the array. In some embodiments, the array 102 also monitors the heart rate variability (HRV) measured through the blood vessels 110 at the area of ear lobe. Although measuring HRV is not necessary for vagus nerve stimulation according to the system provided herein, HRV measurements provide feedback for the array 102. In particular, HRV feedback is used to identify therapeutic patterns of the light and, thus, improve the efficacy of the treatment. HRV feedback also minimizes unwanted side effects by helping target specific vagus branches. An optimal therapeutic pattern is identified when the HRV is within a desired range.

Figure 2:
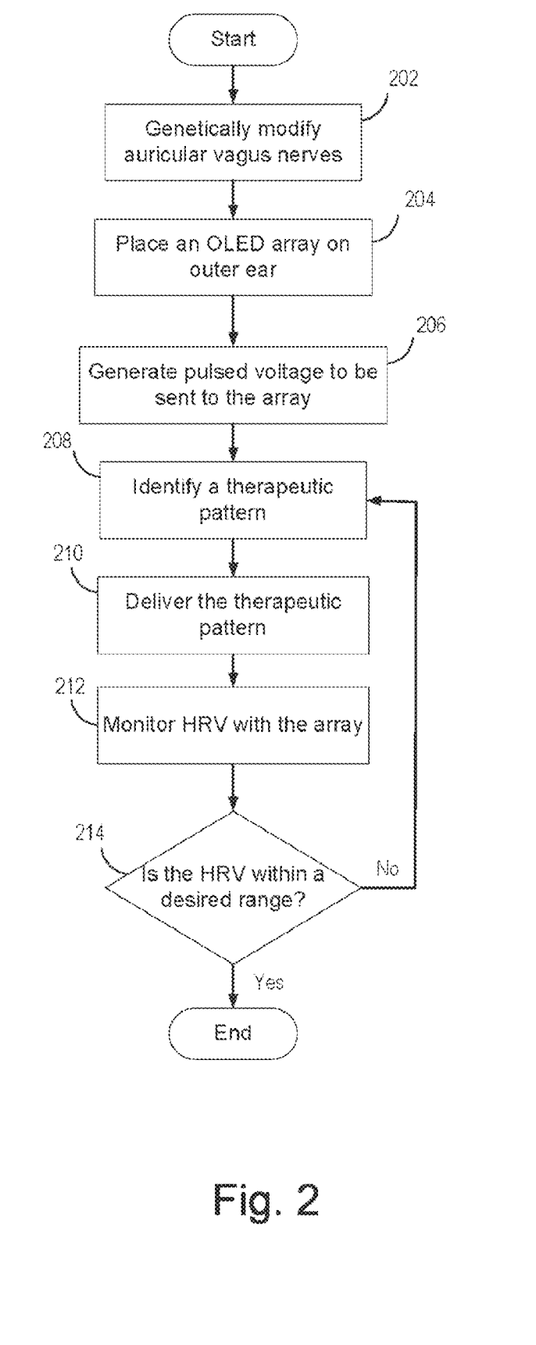
FIG. 2 is a flowchart illustrating an example method implemented in accordance with the present application.

Referring to FIG. 2, a flowchart of a method implemented according to the present application is provided. In step 202, auricular vagus nerves are genetically modified to be sensitive to light. In one embodiment, using a viral vector, auricular vagus nerves are genetically modified to express light-gated ion channels in the cellular membrane which are sensitive to incident light from the OLED array 102. In step 204, an OLED array is placed on the outer ear. The array is flexible so that it can be placed closely on the skin of the outer ear. In step 206, pulsed voltage is generated to power the array so the array generates irradiance strong enough to stimulate the neurons in the auricular vagus nerves. In step 208, a therapeutic pattern is identified. In step 210, the pattern is displayed on the array. In step 212, the array measures and monitors the HRV of blood vessels in the ear lobe. Steps 208 through 212 are repeated until the HRV is within a desired range. This way, the HRV is used as feedback in the process of the array to identify therapeutic patterns of the light emitted from the array.

Figure 3A:
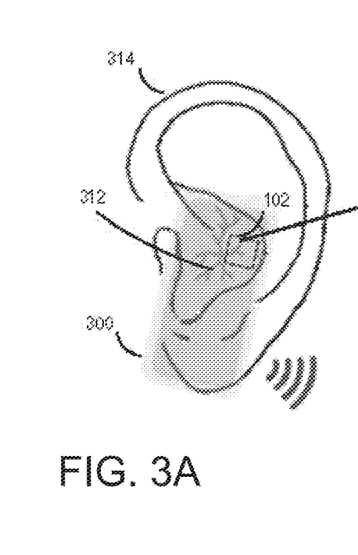
FIG. 3A is a diagram depicting the setup of the system in relation with the vagus nerves.
Figure 3B:
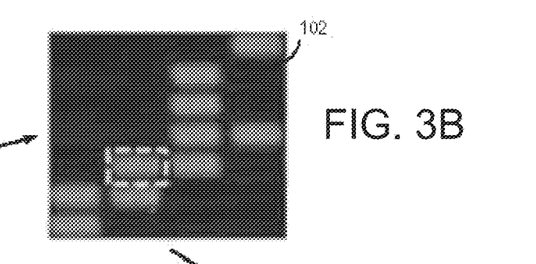
FIG. 3B is a diagram depicting one section of the organic light emitting diodes (OLED) array.
Figure 3C:
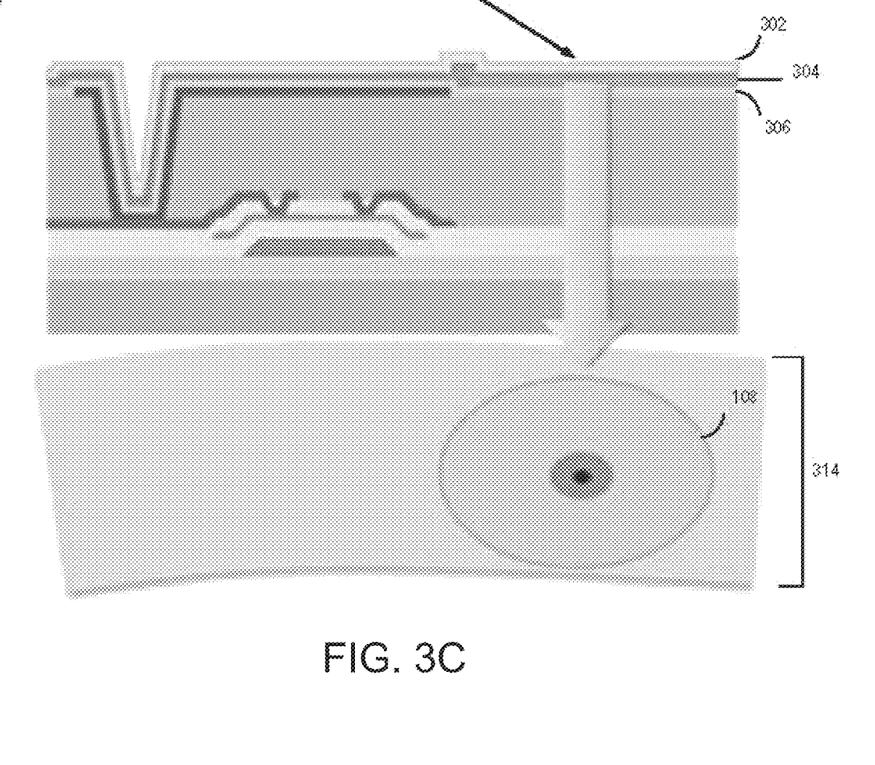
FIG. 3C is a diagram of the structure of an OLED array in relation with the vagus nerve.

Referring to FIG. 3, the array 102 may be incorporated into an array strip 300 positionable on the outer ear as depicted in inset (A). The array 102 is placed behind the auricle 314 and illuminates the vagus nerve 312. The array 102 can be low-cost, disposable, peel-and-stick-like. The array strip 300 incorporating the flexible OLED array 102— similar to an adhesive bandage—can be easily conformed to the outer ear. The array 102 comprises 2D OLED pixels (see inset (B)) and emits light when powered with voltage. The structure of the pixel and the placement of the array 102 in relation with the vagus nerve is depicted in FIG. 3(C). The OLED layer 304 is sandwiched between reflective cathode 302 and transparent anode 306. The pixel emits light behind (see the direction of the arrow in FIG. 3(C)) and the light stimulates an individual auricular vagus nerve 108 in the auricle 314. Longer wavelength red OLED emitters may be preferred because the longer wavelength penetrates skin penetration deeper than shorter wavelength blue light emitted by blue OLED emitters.

Figure 4A:
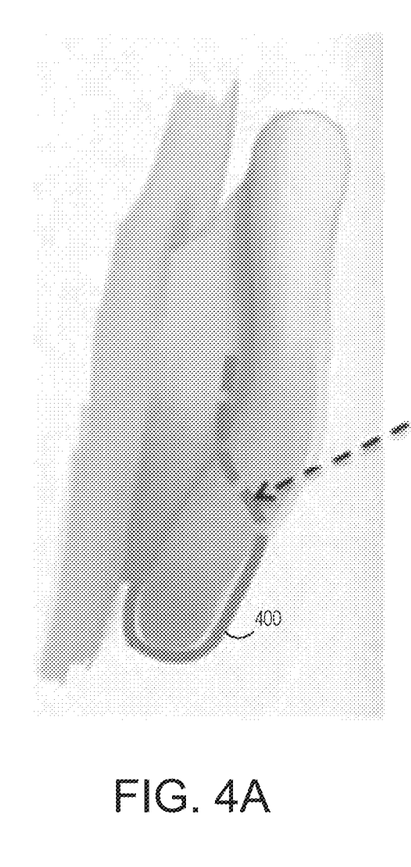
FIG. 4A is a diagram depicting one strip of an OLED array placed on a subject.
Figure 4B:
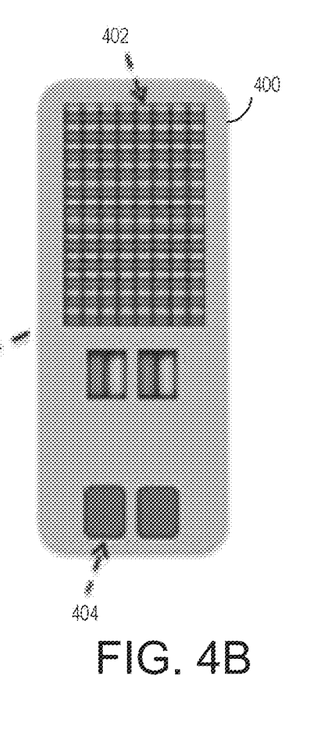
FIG. 4B shows the strip having one section to deliver optical therapeutic patterns and another to monitor hear rate variability simultaneously.

Individual OLED pixels in the flexible OLED display or array 102 can be addressed and turned on to target and selectively illuminate individual auricular vagus nerves in the outer ear. In this manner, OLED pixels of the array are individually addressable. As used herein, the term "individually addressable" means that pixels can be identified and activated or manipulated independently of its surrounding pixels. For example, the phrase "individually addressable" as used herein means that each light component (i.e., an organic light emitting diode (OLED) of the OLED array) can be identified and manipulated independently of its surrounding OLEDs ("individually addressed"). In some cases, each OLED or each group of OLEDs can be individually turned on or off, and output of each OLED or each group of OLEDs can be controlled individually. The OLED array is also called OLED display or display for short because it emits light and can be used to display images. The disposable stick-on flex OLED array 102 is connected to a control unit 104. The control unit 104 can be external battery-powered. It is used to adjust the duration, frequency, and intensity of the transcutaneous optogenetic therapy in real-time, as well as determine which OLED pixels in the 2D array to turn on. This setup allows the optogenetic stimulus pattern or shape (i.e., activated OLED pixels) to be reconfigurable on-the-fly and adaptable to physiological changes. As illustrated in FIG. 4, because the pixels 402 can be individually addressed, the reconfigurable optical stimulus pattern can illuminate one particular auricular vagus nerve branch, and not illuminate (i.e., optically stimulate) neighboring off-target vagus nerves in the outer ear to provide the desired specificity.

The system as disclosed in the present application monitors physiological state and uses the data on physiological state to identify optimal therapeutic patterns of the light. The system and method disclosed herein includes a real-time noninvasive method to monitor vagus nerve activity by monitoring HRV using an OLED-based optical heart rate monitor (OHRM). Vagus nerve activity, with a particular attention to HRV, can be correlated with anti-inflammatory activity. Flexible OLED and photodiode sensor technology can be applied to measure pulse rate and arterial blood oxygenation. HRV is measured using a flexible OLED illumination source combined with a flexible photodiode— integrated on the same disposable bandage-like flex substrate as the 2D optogenetic OLED array. As shown in FIG. 4, insets (A-B), the array strip 400 is placed behind the auricle and wrapped around the lobe with photodiode sensors 404 and the pixels 402 on opposite sides of the lobe. OLED pixels 402 illuminate blood vessels in the ear lobe and the modulated optical signal is then detected by opposing flex photodiode sensors 404 stuck to the other side of the ear lobe. The objective is to create a closed-loop feedback system—integrated on the same disposable VNS bandage for real-time optical-based vagus stimulus and sensing. In one configuration, immediately after applying the optogenetic VNS bandage, an optical search pattern is activated and the OLED-based VNS optogenetic array cycles through a series of patterns (i.e., activated pixels) while simultaneously monitoring HRV to identify and lock-in the optimal therapeutic pattern.

The system and method disclosed herein can monitor vagus nerve stimulation in real time using photoplethysmography (PPG). Optical heart rate monitoring or PPG detects changes in blood volume using an optical transmission or reflection probe. Changes in blood volume in the peripheral vascular system, such as in the earlobe, are directly linked to the activity of the heart. With this direct relation, an on-skin or intra-ear optical PPG sensor can replace conventional multiple electrode-based ECG methods to accurately measure the heart rate. In addition, the PPG signal is sensitive to vasodilation, which can be detected via the particular shape of the PPG signal.

PPG signals can be acquired using an optical transmission probe, similar to a pulse oximeter. The wavelength of the light, however, should be outside of the range sensitive to the blood oxygenation in order to maintain selectivity of the PPG signal. Because most pulse oximeter probes contain a reference sensor, the reference sensor signal can be used for PPG. Alternatively, a reflection-based setup can be used to measure PPG, which allows for a greater design freedom and enables probes to be attached to in-ear headphones that are inserted into the ear canal. In addition, signal processing of the PPG signal allows the separation of low-frequency drift components and, with a spectral decomposition, the extraction of respiratory rate signals and signals related to the mechanical compliance of the vascular system. Thus, the PPG signal provides rich information such that PPG can replace ECG monitoring.

Figure 5:
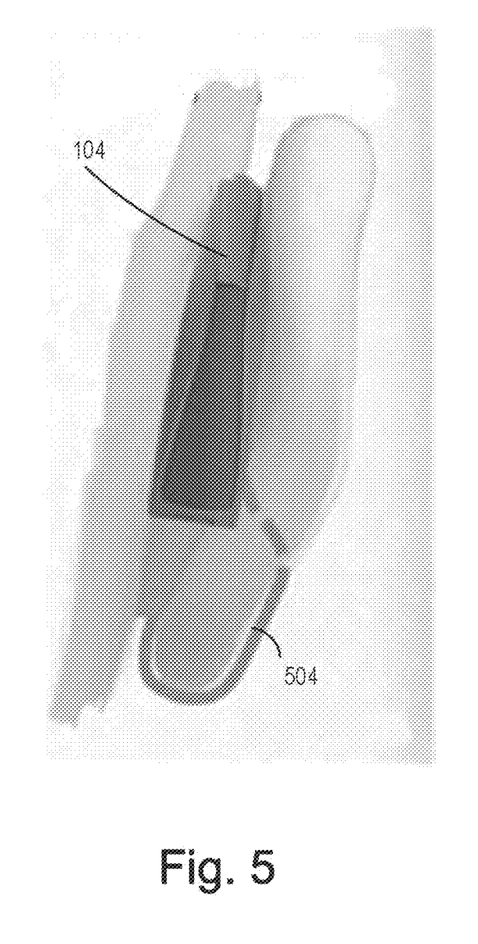
FIG. 5 is a schematic diagram of placement of an example system that is insensitive to motion.

While the heart rate can be measured directly via PPG, the PPG signal is prone to motion artifacts. This is due to the particular mounting configuration of an optical transmission or reflection sensor, for example ear-clip or ear canal sensors. The motion artifacts can trigger false positive events when the PPG signal is embedded in an autonomous feedback loop. But the motion artifacts can be suppressed by using a secondary sensor, such as a microelectromechanical system (MEMS) accelerometer, that tracks the motion of the optical sensor. By subtracting the motion-related signal component, the PPG signal can be recovered even during physical exercise routines. In one configuration, a MEMS-based accelerometer is integrated with an external control unit positioned behind the ear—similar to a hearing aid. As shown in FIG. 5, a MEMS-based accelerometer is integrated in the control unit 104 and placed behind the ear like a hearing aid. The PPG signals are acquired through the flex OLED array 504 and then digitized for process with a digital signal processing algorithm to extract signal components relevant to vagus neural stimulation.

A PPG-based optical neuromodulation monitor can be implemented using the flexible OLED and photodiode sensor integrated on the same substrate with the 2D optical OLED array for optogenetic neuromodulation. This integration is possible because of the physical separation between the blood vessels in the ear lobe and the targeted vagus nerves in the outer ear. This allows the OLEDs to be used simultaneously for both vagus nerve optical modulation and optical heart rate monitoring, and thus a continuous real-time autonomous feedback-loop is provided during patient therapy.

Figure 6:
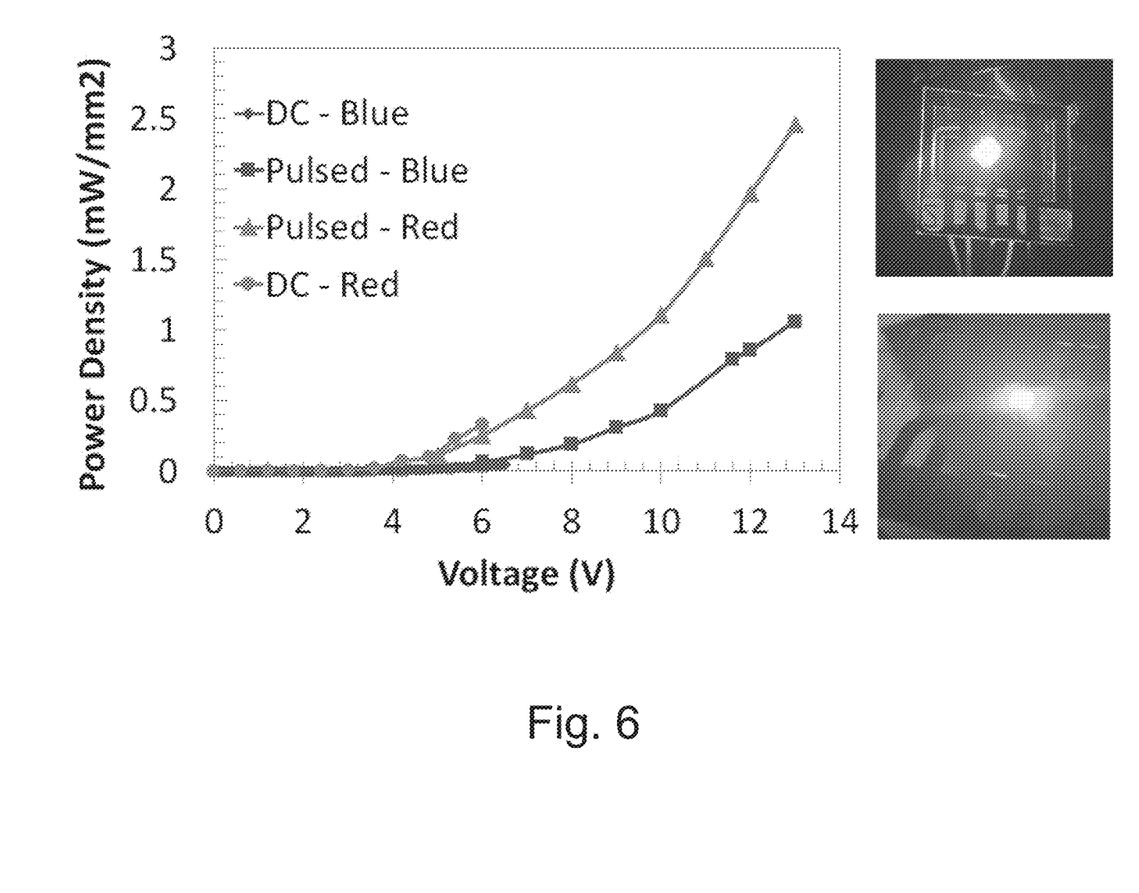
FIG. 6 is a plot of power density of the irradiance generated by the array as a function of forward bias voltage applied to the array.

For the light emitted from the array to have high enough power density to control the neurons, the power delivered to the array is pulsed. A minimum of 1 mW/mm$^2$ of instantaneous pulsed irradiance at a wavelength of ~450 nm is required to induce optical stimulation in ChR2 expressing neurons. Referring to FIG. 6, comparison between the standard power density (PD) curve 602 and the PD curve 604 of pulsed voltage is provided using a bottom emitting 455 nm blue OLED. As shown in standard PD curve 602, a big increase in the operating voltage is needed to cause a small change in the PD. To make matters worse, increasing the direct current (DC) bias above 7 V—a typical bias condition and intensity for a commercial flat panel OLED display—to obtain higher light intensity can degrade the OLED organic emission layers due to current induced, localized joule heating in the OLED organic layers (see the absence of data points beyond 6.5 V of curve 602). On the other hand, if pulsed voltage is used as shown in curve 604, increasing the voltage across an OLED can exponentially increase current, which in turn causes exponential increase in the OLED light intensity. Such a behavior is similar to a semiconductor diode. Also, the increase of operating voltage does not degrade or damage the OLED organic layers. Pulsing the OLED power supply at 20 Hz, along with attaching a thin and flexible metal foil cathode heat sink, allowed us to increase the OLED bias voltage to 13 volts. This provided a 10× boost in instantaneous blue light intensity from 0.1 mW/mm$^2$ (under DC bias) to 1 mW/mm$^2$ (pulsed-mode) without degrading or damaging the OLED organic layers (FIG. 6). With pulse voltage, PD can be over 1000 A/cm$^2$.

The system and method disclosed herein may use a heat sink to dissipate the heat in the array. With the increased PD, heat builds up in the array from the high current. One mechanism to dissipate the heat is to use a substrate with high thermal conductivity. Another mechanism is to use a thin conformal heat sink, such as a thin metal foil, to keep the device temperature low while maintaining flexibility of the array. In addition, pulsed voltage of short pulse width and at a low frequency allows the organic layers in the OLED to cool down before a voltage bias is applied in the next period. Referring again to FIG. 6, the required 1 mW/mm$^2$ of instantaneous light intensity is achieved using pulsed voltage at 13 volt of 20 Hz with a 10 ms pulse width.

The OLED array disclosed herein is flexible so that it can be placed closely to the skin of a subject. It is a very thin and transparent sheet of plastic, approximately the same thickness as a sheet of paper and constructed by sequentially layering and patterning nanoscale thin films. This approach of construction allows the electronics functionality to be built or integrated directly into plastic substrates using active thin film devices such as OLED emitters, PIN photodiodes, and thin film transistors, other than separately bonding a large number of discrete electronic components. This approach can take advantage of commercial flat panel display technology, which can manufacture displays on Gen11-sized glass substrates that approach 10 m 2. This can reduce un-functionalized sensor costs to pennies per cm$^2$, which is key for low-cost disposable applications. More importantly, the flat panel display industrial base is well established and capable of annually supplying the massive numbers of large-area electronics components required to rapidly transition this technology from the laboratory to a low cost consumer product.

Figure 7:
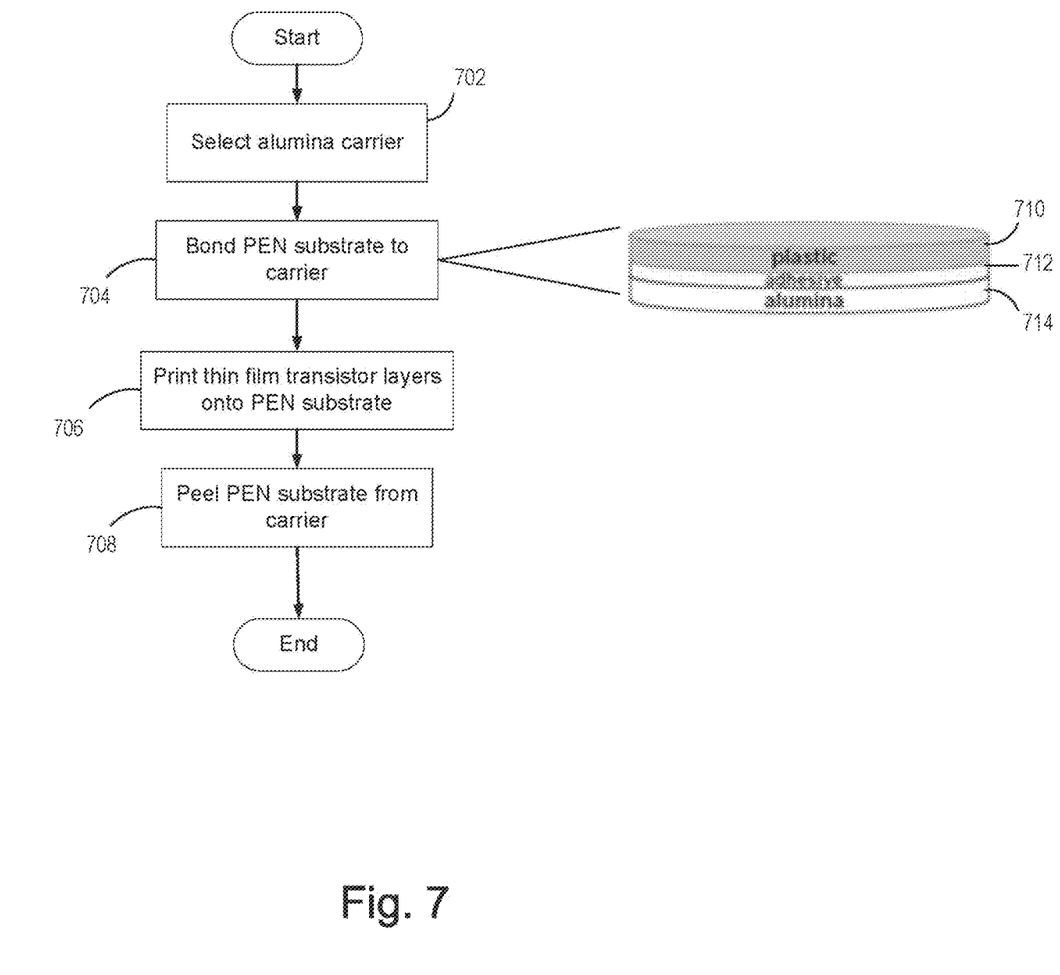
FIG. 7 is a flowchart depicting an example process to manufacture a flexible array.

Example processes to manufacture flexible OLED array are as follows. The flexible display manufacturing process is similar to the process used to manufacture large commercial flat-panel LCD displays on glass substrates. To make the device flexible, the starting glass substrate—such as a 125 μm thick DuPont Teijin Films Teonex® polyethylene naphthalate (PEN) flexible plastic substrate—is flexible. Referring to FIG. 7, example processes implemented according to the present application is provided. In step 702, a 6" rigid alumina carrier is chosen. In step 704, flexible PEN plastic substrate 710 is bonded with alumina carrier 714 through adhesive 712. In step 706, low temperature (<200° C.) thin film transistor processing is conducted. After the thin film process steps are completed, in step 708, the flexible plastic PEN substrate with patterned thin film layers on top is peeled off, similar to peeling off a Post-it® note. The rigid alumina carrier allows the flexible display to be manufactured using off-the-shelf, thin-film semiconductor process tooling without modification.

In one configuration, polyimide or other flexible material that can tolerate higher temperature than PEN plastic is used if the processing temperature is too high for the substrate. Commercial glass substrate thin film transistors or silicon wafer processing can be >300° C. For PEN plastic substrate, to avoid exceeding the PEN plastic substrate transition temperature so not to melt it, the maximum processing temperature throughout the entire flexible electronics process sequence is limited to a maximum of ~180° C. Polyimide tolerates higher temperature. Also, thinner polyimide can be used as substrate; for example, flexible electronics devices can be manufactured on 20 μm thick polyimide substrates as an alternative to the 125 μm thick PEN plastic substrates. One more advantage of polyimide is that the optogenetic VNS bandage device using polyimide substrates is significantly more flexible than PEN plastic substrates. The polyimide process is similar to PEN except that, instead of bonding the plastic substrate to a carrier using a temporary adhesive, polyimide is dispensed in liquid form directly onto the rigid substrate. The polyimide is then cured at >200° C. to drive out the solvents. At this point the polyimide and the rigid substrate is ready for thin film processing. After the thin film processing is completed, the flexible polyimide substrate with patterned thin film transistor layers on top is peeled off, similar to the debonding of the PEN substrate.

The cost of OLED arrays as disclosed herein can be low through mass production. For example, multiple arrays can be manufactured on a sheet of 370 mm×470 mm gen2 plastic. In one configuration, the transcutaneous VNS OLED array is manufactured on a thin and flexible biocompatible plastic substrate, such as polyimide, using conventional thin-film display technology. This approach of manufacturing takes advantages of the scale of commercial flat panel array technology to reduce pre-functionalized costs to pennies per square centimeter ($cm^2$), and a well-established industrial base capable of annually supplying an immense number of consumer electronic products that can be readily adapted to produce hundreds of millions of peel-and-stick disposable transcutaneous VNS devices per year. For perspective, flat panel displays were manufactured at a rate of 100 square kilometers per year in 2012. If just one percent (1%) of existing flat panel industrial capacity was diverted to manufacture flexible bioelectronic devices, approximately 1 billion (~10 cm2) bioelectronic arrays could be manufactured annually. As the cost is low and supply is plenty, the array can be cheap enough to consumers to be disposable. Such disposable OLED-based optogenetic VNS stimulators can be manufactured on large table-top sized multi-device sheets that can then be cut up into the much smaller individual low cost disposable devices. Additionally, instead of using a conventional monochromatic light source, OLED arrays can display in multiple colors. This allows for localized and addressable optical control of the neurons using one color for activation and a different color for inhibition in the same array. Alternatively, combinations of red, green, and blue (RGB) OLED pixels in the array can be activated to locally reproduce the entire color spectrum, similar to a conventional full color flat panel display.

Figure 8:
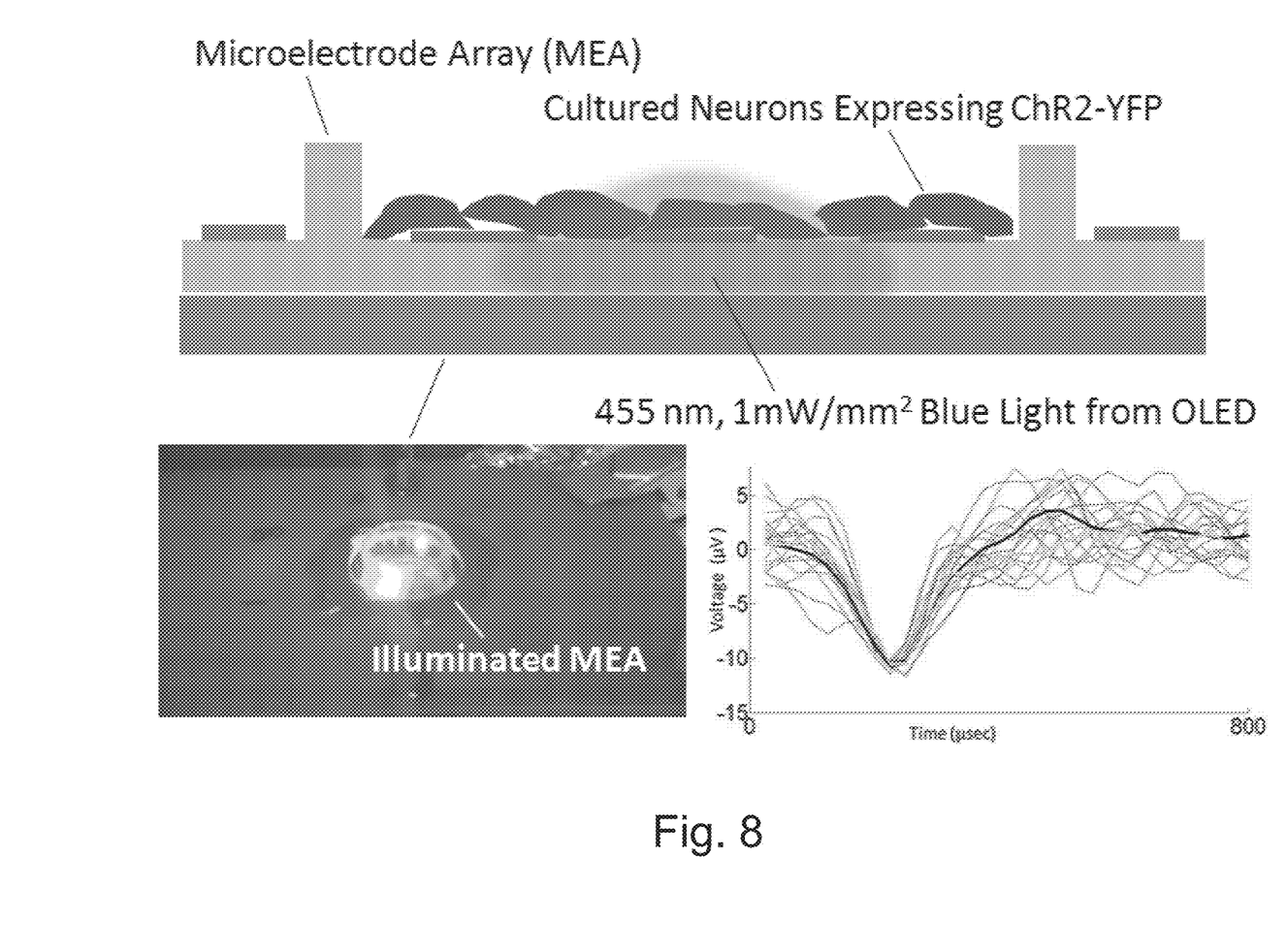
FIG. 8 illustrates an experimental test configuration for optical stimulation of cultured neurons in vitro. A 32 channel microelectrode array (MEA) connected to Intan neural recording system was used to demonstrate that 1 mW/mm$^2$ of pulsed 455 nm light from blue OLED test structure can optically stimulate cultured neurons in vitro using cells expressing ChR2-YFP. Time aligned neural spike activity under blue OLED optical stimulation. Green and black waveforms are the mean values of all recordings captured before (green waveform) and after (black waveform) optical stimulation.
Figure 9:
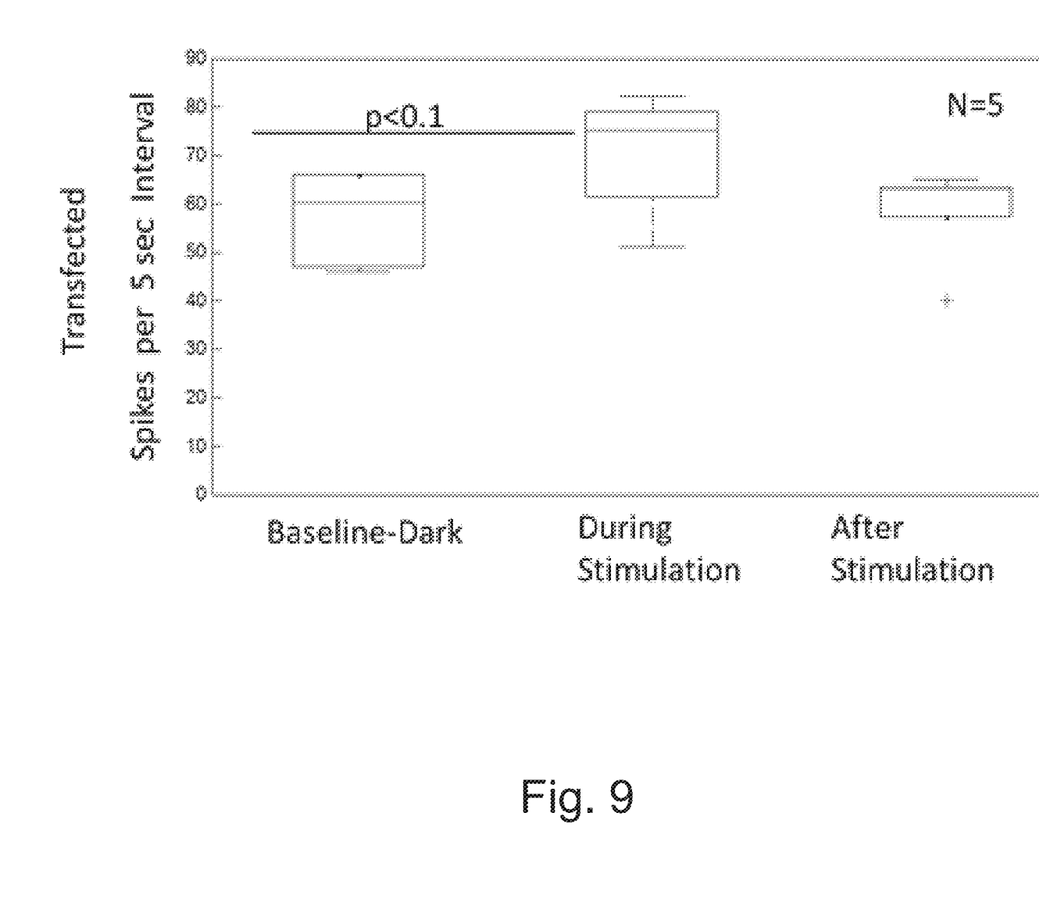
FIG. 9 is a plot of optical stimulation data for primary cortical E18 neurons in culture transfected with ChR2-YFP gene. Transfected primary cortical E18 neurons exhibited a statistically significant increase in spike rate when illuminated by pulsed 1 mW/mm$^2$ 455 nm light from the 5 mm$^2$ blue OLED test structure.

In order to determine whether pulsed blue light from an OLED test structure was able optically stimulate cortical neurons in vitro using cells expressing the opsin ChR2-YFP, primary cortical E18 neurons were cultured on the surface of a conventional transparent microelectrode array (MEA). The 5 $mm^2$ blue OLED test structured was then positioned directly underneath the MEA and activated to optically stimulate the cultured neurons using 20 Hz, 1 $mW/mm^2$ pulsed 455 nm blue light (FIG. 8). Electrical activity of the blue OLED photostimulated cortical neurons was monitored and evaluated for correlation with the incident 20 Hz light pulse. As illustrated in FIG. 8 and FIG. 9, the detected spike rate in the neural tissue expressing ChR2-YFP increased when the blue OLED was turned on, and then immediately decreased to baseline values when the blue OLED was turned off. Accordingly, preliminary analysis and optical measurements indicate that our 620 nm flexible red OLED display technology is bright enough to induce therapeutic optical stimulation in optogenetically modified neural tissue.

The present invention has been described in terms of one or more preferred embodiments, and it should be appreciated that many equivalents, alternatives, variations, and modifications, aside from those expressly stated, are possible and within the scope of the invention. The appended document describes additional features of the present invention and is incorporated herein in its entirety by reference.

We claim:

1. A method for non-invasively stimulating an optogenetic vagus nerve of a subject, the method comprising:
    wrapping a flexible substrate of a stimulation and monitoring device around a portion of the subject's ear such as to place an adhesive of the flexible substrate in direct contact with skin of the subject's outer ear and to have a first portion of said flexible substrate contact the subject's ear adjacent to the optogenetic vagus nerve, wherein the device includes:
        said flexible substrate carrying a two-dimensional array of organic light emitting diodes (OLEDs) and one or more photodiode, each disposed on a first surface of the flexible substrate,
        the two-dimensional array of OLEDs being positioned on the first portion of said flexible substrate between a reflective cathode and a transparent anode, the transparent anode being in direct contact with the flexible substrate,
        OLEDs of at least a portion of the array of OLEDs being spaced on the flexible substrate relative to the one or more photodiode such as to oppose other OLEDs when the flexible substrate is wrapped around the portion of the subject's ear,
        the adhesive disposed on an opposing surface relative to the first surface,
    delivering light generated by the OLEDs to the optogenetic vagus nerve and said one of more photodiodes after said light has passed through one or more blood vessels in the subject's ear to monitor heart rate variability (HRV) of the subject with said one or more photodiodes;
    stimulating the optogenetic vagus nerve of the subject with pulsed light generated by the OLEDs by providing pulsed electrical current to the OLEDs from a voltage-generating unit that is in operable communication with said OLEDs, and
    generating an HRV signal indicating a degree of HRV of the subject based on a signal generated by the one or more photodiodes.

2. The method of claim 1, further comprising treating a disorder or condition associated with aberrant vagus nerve activity with said stimulating.

3. The method of claim 2, wherein the treating includes treating the disorder or condition selected from the group consisting of rheumatoid arthritis, systemic inflammatory response syndrome, inflammatory bowel disease, depression, post-traumatic stress disorder (PTSD), anxiety, epilepsy obesity, traumatic brain injury, coma, an addiction disorder, dementia, sleep disorders, pain, and migraine.

4. The method of claim 1, wherein OLED pixels of the array are individually addressable.

5. The method of claim 1, further comprising determining, with a feedback loop of the device, a therapeutic pattern of pulsed light based on monitoring of the HRV, and
wherein said providing pulsed electrical current to the OLEDs includes providing pulsed electrical current with pulses organized in said in a therapeutic pattern.

6. The method of claim 1, further comprising identifying a therapeutic pattern of light stimuli, wherein identifying comprises monitoring the subject's HRV and HRV changes in response to light stimuli.

7. The method of claim 6, wherein, when the method is applied to multiple subjects, the method includes identifying the therapeutic pattern empirically for each of said multiple subjects.

8. The method of claim 1, further comprising:
providing the pulsed electrical current to the OLEDs according to a plurality of stimulation patterns, each stimulation pattern of said plurality defined by one or both of: corresponding amount of current provided to each OLED of the array of LEDs or corresponding temporal illumination patterns of each OLED of the array of OLEDs; and
determining, using values of the HRV signal generated while operating the OLED array according to each of the plurality of stimulation patterns, whether one or more simulation patterns are effective patterns for stimulating the optogenetic vagus nerve; and
wherein the OLED array includes two or more individually addressable portions.

9. The method of claim 8, further comprising repeatedly providing the pulsed electrical current to the OLEDs according to one or more simulation patterns that have been determined to be the effective patterns.

10. The method of claim 1, further comprising using a feedback controller to:
provide the pulsed electrical current to operate the OLEDs according to a stimulation pattern defined by one or both of: an amount of current provided to each OLED of the array of OLEDs or a temporal illumination pattern of each OLED of the array of OLEDs;
calculate a feedback signal indicating a difference between a value of the HRV signal generated when operating the OLEDs according to the stimulation pattern and a desired value of the HRV signal; and
automatically reduce a magnitude of the feedback signal by automatically adjusting the stimulation pattern while operating the OLEDs according to the stimulation pattern.

11. The method of claim 1, wherein OLEDs have transparent top electrodes.

* * * * *